US 8,521,560 B2

(12) United States Patent
Wakayama

(10) Patent No.: US 8,521,560 B2
(45) Date of Patent: Aug. 27, 2013

(54) RELIEF SUPPORT SYSTEM

(76) Inventor: Takuhei Wakayama, Tokyo (JP)

( * ) Notice: Subject to any disclaimer, the term of this patent is extended or adjusted under 35 U.S.C. 154(b) by 0 days.

(21) Appl. No.: 13/484,234

(22) Filed: May 30, 2012

(65) Prior Publication Data

US 2012/0310659 A1 Dec. 6, 2012

(30) Foreign Application Priority Data

May 31, 2011 (JP) ................................. 2011-121645

(51) Int. Cl.
*G06Q 10/00* (2012.01)
*G06Q 50/00* (2012.01)

(52) U.S. Cl.
USPC ....................................... 705/2; 705/3; 705/4

(58) Field of Classification Search
USPC ........................................................ 705/2–4
See application file for complete search history.

(56) References Cited

U.S. PATENT DOCUMENTS

| | | | |
|---|---|---|---|
| 2007/0250348 A1* | 10/2007 | D'Ambrosia et al. ............ | 705/3 |
| 2010/0063846 A1* | 3/2010 | Shakamuri ........................ | 705/3 |
| 2010/0293005 A1* | 11/2010 | Glimp et al. ...................... | 705/2 |

FOREIGN PATENT DOCUMENTS

| | | |
|---|---|---|
| JP | 09-304506 | 11/1997 |
| JP | 1997-304506 | 11/1997 |
| JP | 2006-170751 | 6/2006 |
| JP | 2006-237666 | 9/2006 |
| JP | 2006-263181 | 10/2006 |
| JP | 2009-157485 | 7/2009 |
| JP | 2011-091720 | 5/2011 |
| WO | 2011/024880 | 5/2011 |

OTHER PUBLICATIONS

Webb, Black Boxes, May 12, 2005, EDN, pp. 33-38.*
WO 2011/024880 A1, published on Mar. 3, 2011.

* cited by examiner

*Primary Examiner* — Luke Gilligan

(57) ABSTRACT

A user desiring to check safety of an individual to be rescued can check safety estimation information, medical insurance information, information about a vital sign, and clinical information about an individual via a portable terminal. A system includes a relief database receiving information recorded on a personal medical database and a vital device and recording the information, a safety condition calculating unit calculating safety estimation information where a safety condition of the individual is estimated by comparing the clinical information and the information about the vital sign recorded on the relief database, and a portable terminal accessing the medial insurance information recorded on the relief database, the safety estimation information, and the information about the vital sign and the clinical information recorded on the relief database and displaying the medical insurance information, the safety estimation information, the information about the vital sign, and the clinical information.

6 Claims, 2 Drawing Sheets

RELIEF SUPPORT SYSTEM

CROSS-REFERENCE TO RELATED APPLICATIONS

This application is based on and claims priority from Japanese Patent Application No. 2011-121645, filed on May 31, 2011 in the Japan Patent Office, the disclosure of which is incorporated herein in its entirety by reference.

BACKGROUND OF THE INVENTION

1. Field of the Invention

The present invention relates to a relief support system and, in particular, to a relief support system using information about vital signs.

2. Description of the Related Art

A rescue system using a global positioning system (hereinafter referred to as GPS) has been conventionally known.

For example, a technology is suggested in Japanese Unexamined Patent Application Publication No. 9-304506, in which positional information about a sufferer in a marine accident or the like obtained by a GPS is used to efficiently support rescue activities in a shorter time.

For example, the rescue system described above is provided with a rescue system processing apparatus that automatically selects a rescue boat closest to the absolute position of a GPS receiver received from the sufferer and transmits the positional information about the sufferer to the selected rescue boat to automatically rush the boat to the accident. With this, when the sufferer is in an emergency situation, the most suitable rescue boat can be rushed to the sufferer within a short time.

However, in such an emergency scene, medial information such as an electronic medical chart required for diagnosing the condition of the sufferer himself or herself is not at hand. Therefore, a doctor disadvantageously has to conduct diagnosis and treatment under circumstances where previous diagnosis results of the sufferer cannot be known.

Also, in the case of occurrence of many victims as in the earthquake off the Pacific coast of Tohoku, the number of victims enormously exceeds the number of people that can be rescued by a rescue team, thereby disadvantageously making it difficult to determine which sufferer is to be rescued.

Thus, in view of the circumstances described above, an object of the present invention is to provide a relief support system using information about vital signs and clinical information of a sufferer.

SUMMARY OF THE INVENTION

A relief support system according to an aspect of the present invention includes a personal medical database having recorded thereon personal clinical information or medical insurance information about a plurality of individuals, a personal-mount vital device for measuring a vital sign of each of the individuals and recording information about the measured vital sign, a relief database communicatively connected to the personal medical database and the vital device, the relief database receiving information recorded on the personal medical database and the vital device and recording the information, a safety condition calculating unit calculating safety estimation information in which a safety condition of the individual is estimated by comparing the clinical information and the information about the vital sign recorded on the relief database, and a portable terminal accessing the medial insurance information recorded on the relief database, the safety estimation information calculated by the safety condition calculating unit, and the information about the vital sign and the clinical information recorded on the relief database and displaying the medical insurance information, the safety estimation information, the information about the vital sign, and the clinical information.

The "safety estimation information" is information obtained by estimating a safety condition of an individual and indicates, for example, a time during which life is assumed to be sustained.

In the relief support system of the present invention, the vital device may record at least one or more of a temperature, a respiratory rate, a blood pressure, a heart rate, and electrocardiographic information, may further record positional information of the individuals by a global positioning system, and may regularly transmit the positional information to the relief database, and the relief database may record the transmitted positional information.

The safety condition calculating unit of the relief support system of the present invention may further estimate latest positional information from the positional information recorded on the relief database, and may calculate the estimated safety estimation information from the estimated positional information.

The safety condition calculating unit of the relief support system of the present invention may calculate the safety estimation information by comparing information about a previous vital sign recorded on the relief database and latest vital sign information.

The portable terminal of the relief support system of the present invention may include an input unit inputting cause information about a cause from which an individual is to be relieved, and the safety condition calculating unit may calculate the safety estimation information based on the cause information.

The global positioning system of the vital device of the relief support system of the present invention may be bidirectionally communicable, and the relief database may issue an instruction for receiving the latest positional information, and may receive and record the latest positional information in response to the instruction.

In the relief support system of the present invention, the relief database may further record positional information about a rescue team, the safety condition calculating unit may compare positional information about the rescue team and latest positional information about the plurality of individuals and set a high display priority to safety estimation information about a nearest individual, and the portable terminal may display the safety estimation information in descending order of the display priority.

A relief support system according to another aspect of the present invention includes a personal medical database having recorded thereon personal clinical information or medical insurance information about a plurality of individuals, a relief database communicatively connected to a personal-mount vital device for measuring a vital sign of each of the individuals and recording information about the measured vital sign and the personal medical database, the relief database receiving information recorded on the personal medical database and the vital device and recording the information, a safety condition calculating unit calculating safety estimation information in which a safety condition of the individual is estimated by comparing the clinical information and the information about the vital sign recorded on the relief database, and a portable terminal accessing the medial insurance information recorded on the relief database, the safety estimation information calculated by the safety condition calculating unit, and the information about the vital sign and the clinical information recorded on the relief database and displaying the medical insurance information, the safety estimation information, the information about the vital sign, and the clinical information.

According to the relief support system of the present invention, the system includes a relief database receiving information recorded on a personal medical database and a vital device and recording the information, a safety condition calculating unit calculating safety estimation information in which a safety condition of the individual is estimated by comparing clinical information and the information about the vital sign recorded on the relief database, and a portable terminal accessing the medial insurance information recorded on the relief database, the safety estimation information calculated by the safety condition calculating unit, and the information about the vital sign recorded on the relief database and displaying the medical insurance information, the safety estimation information, and the information about the vital sign. Therefore, a user who desires to check safety of an individual to be rescued can check the safety estimation information, the medical insurance information, and the information about the vital sign via the portable terminal, thereby being able to make an appropriate diagnosis and determination about treatment for rescue. Also, when a plurality of individuals to be rescued are present, an individual to be immediately rescued can be identified by using the safety estimation information.

DETAILED DESCRIPTION OF THE PREFERRED EMBODIMENTS

Figure 1:
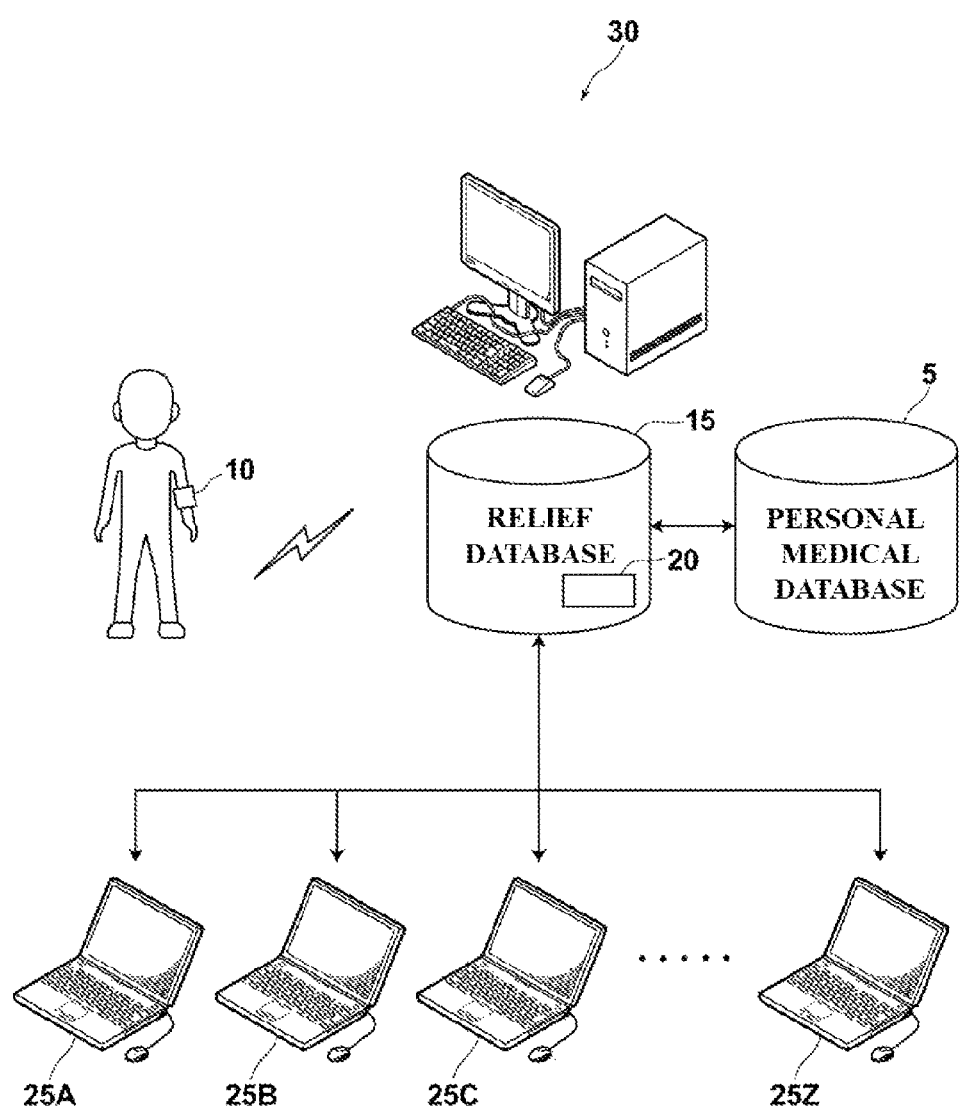
FIG. 1 is a drawing of a relief support system in an embodiment of the present invention.

A relief support system 30 according to an embodiment of the present invention is described with reference to the drawings. The relief support system 30 includes a personal medical database 5 having recorded thereon personal clinical information or medical insurance information about a plurality of individuals, a personal-mount vital device 10 for measuring a vital sign of each of the individuals and recording information about the measured vital sign, a relief database 15 communicatively connected to the personal medical database 5 and the vital device 10, the relief database receiving information (for example, at least one or more of a temperature, a respiratory rate, a blood pressure, a heart rate, electrocardiographic information, heart-rate information, and other information) recorded on the personal medical database 5 and the vital device 10 and recording the information, a safety condition calculating unit 20 calculating safety estimation information in which a safety condition of the individual is estimated by comparing the clinical information and the information about the vital sign recorded on the relief database 15, and a portable terminal 25 accessing the clinical information and the medial insurance information recorded on the relief database, the safety estimation information calculated by the safety condition calculating unit 20, and the information about the vital sign recorded on the relief database and displaying the medical insurance information, the safety estimation information, the information about the vital sign, and the clinical information. This safety estimation information is information obtained by estimating a safety condition of an individual and indicates, for example, like an estimated life sustainable value shown in FIG. 2, a time during which life is assumed to be sustained or a degree of severity and emergency for emergency transfer.

Also, the user can register clinical information about individuals (such as medical chart information and information about drug reaction) in advance in the personal medical database 5 by using a computer via the Internet circuit.

The vital device 10 includes a communicating function, measures a vital sign (at least one or more of a temperature, a respiratory rate, a blood pressure, a heart rate, and electrocardiographic information) of the individuals, and records the measured vital sign. The vital device 10 also records positional information of the individuals by a GPS, and regularly transmits the positional information to the relief database 15. Furthermore, the vital device 10 may transmit the positional information to the relief database 15 through an operation by the user. The relief database 15 then records the positional information transmitted from the vital device 10.

Also, the vital device 10 may include a positional information obtaining function described in Japanese Unexamined Patent Application Publication No. 2006-185436 and, even when satellite communication is interrupted, the vital device 10 can calculate estimated positional information by calculating history data regarding positional information (such as a cumulative footstep count) and weather and geographic information with a computer and then transmit the positional information to the relief database 15. Furthermore, the GPS of the vital device 10 may be bidirectionally communicable, and the relief database may issue an instruction for receiving the latest positional information, and may receive and record the latest positional information in response to the instruction.

The vital device 10 can be used to get medical insurance (for example, mountain insurance, life insurance, and others in the case of mountaineering) wirelessly via the Internet circuit through an operation by the user. This medical insurance information obtained by the vital device 10 is recorded on the personal medical database 5. Note that this medical insurance information may contain signature information indicating prior consent of the user regarding disclosure of information to doctors and medical facilities at the time of an accident or sudden illness.

Still further, the vital device 10 can record a set value of a vital sign of the user in advance, and calculate and process a differential value between the set value and the measured value of the vital sign.

When this calculated differential value is large, the vital device 10 uses wireless communications (such as the Internet or a telephone circuit) to transmit the information about the vital sign, the differential value, the set value, and the positional information to the personal medical database 5.

Still further, the vital device 10 can set various modes. For example, it is possible to select a mountaineering mode (hiking mode), a snowy mountain mode, a seniors mode, and a normal mode assuming disasters such as tsunami. Depending on each of the various modes, information transmitting timing and the transmission destination described above can be set differently. Also, the vital device 10 may include a touch panel function.

Still further, the vital device 10 can transmit, to the relief database 15, personal name information, calling state (whether calling is available or not), declaration details (for example, when the mountaineering mode is selected, a declaration of a hard chest blow or the like), and information about contact address.

Still further, the vital device 10 may have a function of measuring a vital sign and a GPS function separately. In this case, a vital-sign measuring function device may use short-distance wireless communication and a short-range communication network. Also, similarly, a GPS function device may use short-distance wireless communication and a short-range communication network.

The personal medical database 5 can request continuous transmission of information about a vital sign from the vital device 10 according to the physical condition of the user to update the information. Furthermore, upon reception of a notification of prediction indicating a disaster forecast, the personal medical database 5 requests an increase in frequency of transmission of information about a vital sign from the vital device 10 to update the information.

The personal medical database 5 can compare the information about the vital sign registered in advance by the user and information about a vital sign measured by the vital device 10 to determine validity of these pieces of information. Also, the personal medical database 5 can transmit clinical information, medical insurance information, and positional information regarding which prior consent has been obtained in advance from the user to the relief database 15 or the portable terminal 25 provided in a medical facility, a medical emergency center, an emergency organization, a relief organization, a nursing home, an emergency headquarters in the Self-Defense Forces, police, or fire authorities.

The relief database 15 includes a function capable of notifying an insurance company when the situation of damage of the user matches the policy conditions of insurance.

The portable terminal 25 implemented as a computer can request a dispatch for emergency rescue and make arrangements for hospital acceptance, based on the information obtained from the relief database 15. Also, the portable terminal 25 can obtain information about a user on which the vital device 10 is mounted, and therefore a treatment can be smoothly performed by doctors at a facility provided with the portable terminal 25.

Also, in that facility, from the medical information reported in advance, the state of insurances the user has, such as health insurance and mountain insurance, can be known. Therefore, only when the situation of damage of the user matches the policy conditions of insurance, an inquiry to the insurance company and a charge can be made without making an inquiry to the user.

The safety condition calculating unit 20 compares the clinical information (such as an electronic medical chart) recorded on the relief database 15 and the information about the vital sign measured by the vital device 10, judges that the condition is abnormal when a difference therebetween is large, and judges that the condition is normal when the difference is small.

For example, in the case of the heart rate, the safety condition calculating unit 20 judges a difference between a normal heart rate described in the electronic medical chart and a heart rate measured by the vital device 10.

Figure 2:
FIG. 2 is a drawing of an example of a screen to be displayed on a portable terminal of the present invention.

By using various information recorded on the relief database 15, in light of severity and emergency diagnostic criteria for emergency transfer, the safety condition calculating unit 20 calculates safety estimation information regarding severity and emergency as shown in FIG. 2. The severity and emergency diagnostic criteria are obtained by databasing diagnostic criteria such as "Project Aided by Japan Municipal Development Corporation in 2003, "Report by Committee of Creating Severity and Emergency Diagnostic Criteria for Emergency Transfer", Foundation for Ambulance Service Development, 2004".

The safety condition calculating unit 20 can make a determination regarding triage, where many victims at the same site are classified based on the severity and emergency.

Note that if receiving information in the mountaineering mode from the vital device 10, the safety condition calculating unit 20 makes a judgment in consideration of a possible difference in the heart rate at the time of normal mountaineering.

The safety condition calculating unit 20 measures the latest positional information from the positional information recorded on the relief database 15, and calculates safety estimation information estimated from the estimated positional information.

For example, from information about a travelling track of the positional information (for example, a point A and a point B) of the individual measured by the vital device 10 and cartographic information recorded on the relief database 15, the safety condition calculating unit 20 can make a calculation for estimating a next point (for example, a point C) from a road along the track of travelling.

The safety condition calculating unit 20 can calculate safety estimation information by comparing the information about a previous vital sign recorded on the relief database 15 and the latest vital sign information recorded on the relief database 15 (or the personal clinical database 5).

For example, as shown in FIG. 2, the safety condition calculating unit 20 records information about the vital sign for each elapsed time, compares information about a previous vital sign and information about the latest vital sign among the vital signs for each elapsed time, judges whether the condition is abnormal, and calculates an estimated life sustainable value.

The portable terminal 25 (for example, a notebook personal computer) can display information recorded on the relief database 15. For example, the portable terminal 25 displays a screen as shown in FIG. 2. The portable terminal 25 includes an input unit (for example, a mouse or a keyboard) inputting cause information about a cause from which an individual is to be relieved (mountaineering, snowy mountain, seniors, tsunami, or earthquake). Also, the safety condition calculating unit 20 may accept the cause information inputted by the input unit and calculate safety estimation information based on the cause information.

For example, when information indicating mountaineering is inputted, the portable terminal 25 displays information about mountain insurance, and further displays safety estimation information (for example, an estimated life sustainable value) in the case of mountaineering, as shown in FIG. 2. In the relief support system 30 of the present invention, the relief database further records positional information of a rescue team, the safety condition calculating unit 20 compares positional information about the rescue team and the latest positional information about the plurality of individuals and sets a high display priority to safety estimation information about a nearest individual, and the portable terminal displays the safety estimation information in descending order of the display priority. For example, as shown in FIG. 2, when Mr. XX is near helicopter coordinates of a helicopter of the rescue team and when Mr. YY who is in a condition more severe than Mr. XX is 20 km away from the helicopter coordinates, a high priority is set to Mr. XX. With this, in the case of a major disaster such as tsunami, it is possible to display individuals in the order in which the rescue team can rescue more easily, based on the safety estimation information. Note that if Mr. XX described above is clearly in a lightly-wounded condition, a high priority is set to Mr. YY determined as being in a severe condition based on the safety estimation information.

Also, the portable terminal 25 can display neighborhood hospitals based on the positional information, as shown in FIG. 2.

The relief support system 30 includes the personal medical database 5 having recorded thereon personal clinical information or medical insurance information about a plurality of individuals, the relief database 15 communicatively connected to the personal-mount vital device 10 for measuring a vital sign of each of the individuals and recording information about the measured vital sign and the personal medical database 5, the relief database receiving information (for example, medical information information about the vital sign, medical insurance information, clinical information, and others) recorded on the personal medical database 5 and the vital device 10 and recording the information, the safety condition calculating unit 20 calculating safety estimation information in which a safety condition of the individual is estimated by comparing the clinical information and the information about the vital sign recorded on the relief database 15, and the portable terminal 25 accessing the medial insurance information recorded on the relief database 15, the safety estimation information calculated by the safety condition calculating unit 20, and the information about the vital sign and the clinical information recorded on the relief database 15 and displaying the medical insurance information, the safety estimation information, the information about the vital sign, and the clinical information. Also, the portable terminal 25 may be installed for each facility, and a plurality of portable terminals (25A to 25Z) may be provided. Furthermore, the relief database 15 may be cloud-designed, and can be accessed by a plurality of portable terminals.

The safety condition calculating unit 20 may be configured in the relief database 15, or may be implemented as a separate computer. Note that even if the safety condition calculating unit 20 is implemented as a separate component, the safety condition calculating unit 20 can bidirectionally communicate with the relief database 15.

While the portable terminal 25 is exemplarily implemented as a notebook personal computer in the description above, the portable terminal 25 may be implemented as a desktop personal computer, a portable telephone, or a portable personal computer including a communicating function.

According to the relief support system 30 in the embodiment of the present invention, the system includes the relief database 15 receiving information recorded on the personal medical database 5 and the vital device and recording the information, the safety condition calculating unit 20 calculating safety estimation information in which a safety condition of the individual is estimated by comparing clinical information and the information about the vital sign recorded on the relief database 15, and the portable terminal 25 accessing the medial insurance information recorded on the relief database, the safety estimation information calculated by the safety condition calculating unit, and the information about the vital sign and the clinical information recorded on the relief database 15 and displaying the medical insurance information, the safety estimation information, and the information about the vital sign. Therefore, a user who desires to check safety of an individual to be rescued can check the safety estimation information, the medical insurance information, the information about the vital sign, and the clinical information via the portable terminal, thereby being able to make an appropriate diagnosis and determination about treatment for rescue. Also, when a plurality of individuals to be rescued are present, an individual to be immediately rescued can be identified by using the safety estimation information.

What is claimed is:

1. A relief support system comprising:
a personal medical database having recorded thereon information including personal clinical information and medical insurance information about a plurality of individuals;
a personal-mount vital device configured to measure a vital sign of each of the individuals, and to record information about the measured vital sign;
a relief database communicatively connected to the personal medical database and the vital device, the relief database configured to receive and record the information recorded on the personal medical database and the information recorded on the vital device;
a safety condition calculating unit configured to calculate safety estimation information in which a safety condition of the individual is estimated by comparing the clinical information and the information about the vital sign recorded on the relief database; and
a portable terminal configured to access the medical insurance information recorded on the relief database, the safety estimation information calculated by the safety condition calculating unit, the information about the vital sign, and the clinical information recorded on the relief database, the portable terminal being configured to display the medical insurance information, the safety estimation information, the information about the vital sign, and the clinical information, wherein:
the relief database is further configured to record positional information about a rescue team,
the safety condition calculating unit is configured to compare the positional information about the rescue team and latest positional information about the plurality of individuals, and to set a high display priority to safety estimation information about a nearest individual, and
the portable terminal is configured to display the safety estimation information in descending order of the display priority and, when determining that a condition is severe based on the safety estimation information, to set the display priority higher.

2. The relief support system according to claim 1, wherein:
the vital device is configured to record at least one or more of a temperature, a respiratory rate, a blood pressure, a heart rate, and electrocardiographic information, and is further configured to record positional information of the individuals by a global positioning system, and regularly transmit the positional information to the relief database, and
the relief database is configured to record the transmitted positional information.

3. The relief support system according to claim 1, wherein:
the safety condition calculating unit is configured to calculate the safety estimation information by comparing information about a previous vital sign recorded on the relief database and latest vital sign information.

4. The relief support system according to claim 2, wherein:
the global positioning system of the vital device is bidirectionally communicable, and the relief database is configured to issue an instruction for receiving the latest positional information, and to receive and record the latest positional information in response to the instruction.

5. The relief support system according claim 1, wherein:
based on information about a travelling track of the positional information of the individual calculated by the vital device and based on cartographic information recorded on the relief database, the safety condition calculating unit is configured to make a calculation for estimating a next point from a road along the travelling track.

6. A relief support system comprising:

a personal medical database having recorded thereon information including personal clinical information and medical insurance information about a plurality of individuals;

a relief database communicatively connected to a personal-mount vital device for measuring a vital sign of each of the individuals and configured to record information about the measured vital sign and the personal medical database, the relief database being configured to receive and record the information recorded on the personal medical database and the vital sign from the vital device;

a safety condition calculating unit configured to calculate safety estimation information in which a safety condition of each of the individuals is estimated by comparing the clinical information and the information about the vital sign recorded on the relief database; and a portable terminal configured to access the medical insurance information recorded on the relief database, the safety estimation information calculated by the safety condition calculating unit, the information about the vital sign, and the clinical information recorded on the relief database, the portable terminal being configured to display the medical insurance information, the safety estimation information, the information about the vital sign, and the clinical information, wherein:

the relief database is further configured to record positional information about a rescue team, the safety condition calculating unit is configured to compare the positional information about the rescue team and latest positional information about the plurality of individuals, and set a high display priority to safety estimation information about a nearest individual, and the portable terminal is configured to display the safety estimation information in descending order of the display priority and, when determining that a condition is severe based on the safety estimation information, to set the display priority higher.

\* \* \* \* \*